US007816368B2

(12) United States Patent
Bourrie et al.

(10) Patent No.: US 7,816,368 B2
(45) Date of Patent: Oct. 19, 2010

(54) PYRIDOINDOLONE DERIVATIVES SUBSTITUTED IN THE 3-POSITION BY A HETEROCYCLIC GROUP, THEIR PREPARATION AND THEIR APPLICATION IN THERAPEUTICS

(75) Inventors: Bernard Bourrie, Saint-Gely-du-Fesc (FR); Pierre Casellas, Montpellier (FR); Jean-Marie Derocq, Murviel les Montpellier (FR); Samir Jegham, Montferrier-sur-Lez (FR); Yvette Muneaux, Les Matelles (FR)

(73) Assignee: sanofi-aventis, Paris (FR)

( * ) Notice: Subject to any disclaimer, the term of this patent is extended or adjusted under 35 U.S.C. 154(b) by 0 days.

(21) Appl. No.: 12/252,647

(22) Filed: Oct. 16, 2008

(65) Prior Publication Data
US 2009/0042924 A1 Feb. 12, 2009

Related U.S. Application Data

(63) Continuation of application No. 11/109,121, filed on Apr. 19, 2005, now Pat. No. 7,456,193, which is a continuation of application No. PCT/FR03/03111, filed on Oct. 21, 2003.

(30) Foreign Application Priority Data
Oct. 23, 2002 (FR) .................... 02 13270

(51) Int. Cl.
A61K 31/44 (2006.01)
(52) U.S. Cl. ...................... 514/290; 514/292
(58) Field of Classification Search .............. 514/292, 514/290
See application file for complete search history.

(56) References Cited

U.S. PATENT DOCUMENTS

| 4,263,304 | A | 4/1981 | Ishizumi et al. |
| 4,835,160 | A | 5/1989 | Bisagni et al. |
| 5,880,126 | A | 3/1999 | Skuballa et al. |
| 6,503,888 | B1 | 1/2003 | Kaplitt et al. |
| 6,967,203 | B2 | 11/2005 | Bourrie et al. |
| 7,390,818 | B2 | 6/2008 | Bourrie et al. |
| 2002/0156016 | A1 | 10/2002 | Minuk |
| 2004/0122036 | A1 | 6/2004 | Bourrie et al. |
| 2007/0129365 | A1 | 6/2007 | Bourrie et al. |
| 2008/0214538 | A1 | 9/2008 | Bourrie et al. |

FOREIGN PATENT DOCUMENTS

| EP | 9708409 | * | 3/1997 |
| FR | 2 003 999 | | 11/1969 |
| FR | 2 765 581 | | 1/1999 |
| FR | 2 765 582 | | 1/1999 |
| GB | 1 268 772 | | 3/1972 |
| SU | 833971 | | 5/1981 |
| WO | WO 99/51597 | | 10/1999 |
| WO | WO 01/09129 | | 2/2001 |
| WO | WO 02/087574 | | 11/2002 |
| WO | WO 02/087575 | | 11/2002 |
| WO | WO 2004/041817 | | 5/2004 |
| WO | WO 2005/108398 | | 11/2005 |
| WO | WO 2007/045758 A1 | | 4/2007 |

OTHER PUBLICATIONS

Nicholson-Guthrie et al., Cancer Letters, (2001) pp. 27-30.*
Goodman and Gilman Pharm. 9th Ed. Pharmacological Basis of Therapeutics (1996) pp. 1225-1232 and p. 1269-1271.*
Cecil Text book of Medicine 20th Edition (1997) pp. 1002-1009.*
Jaworska et al., Review of Methods for Assesing the Applicability domains of SARS and QSARS, ( Sep. 2004), 1-8.*
U.S. Appl. No. 12/100,079, filed Apr. 9, 2008, Muneaux et al.
Estenne et al, Derwent Patent Abstract No. 199909 (2003), (Abstract of FR 2 765 582).
Furihata, C., et al., In Vivo Short-Term Assays For Tumor Initiation And Promotion In The Grandular Stomach Of Fischer Rats, Mutation Research, (1995), vol. 339, No. 1, pp. 15-35.
Furihata, C., et al., Unscheduled DNA Synthesis In Rat Stomach-Short-Term Assay Of Potential Stomach Carcinogens, Banbury Report, (1982), vol. 13, pp. 123-135.
Goldman M.D., et al., Cecil, Textbook of Medicine, 21st edition, vol. 1, published 2000 by W.B. Saunders Co. (PA), pp. 1060-1074.
Golovko, T., et al., A New Approach To The Synthesis Of Functionally-Substituted Pyrido 2, 3-D Indoles, Mendeleev Communications, (1995), vol. 6, pp. 226-227.
Goodman & Gilman, Section X. Chemotherapy of Neoplastic Diseases, Goodman & Gilman's the Pharmacological Basis of Therapeutics, 9th Ed., (1996) pp. 1225-1232 and pp. 1269-1271.
Kelland, of Mice and Men: Values and Liabilities of the Athymic Nude Mouse Model in Anticancer Drug Development, Abstract—Eur J Cancer. Apr. 2004; 40(6); pp. 823-836.
Molina, P., et al., Annulation Of Pyridine To Indole By A Tandem Aza-Wittig/Electrocyclization Strategy: Synthesis Of Pyrido 2, 3-B Indoles, Synthesis, (1989), vol. 11, pp. 878-880.

(Continued)

Primary Examiner—Michael G Hartley
Assistant Examiner—Shirley V Gembeh
(74) Attorney, Agent, or Firm—Kelly L. Bender; R. Brian McCaslin

(57) ABSTRACT

The present disclosure relates to pyridoindolone derivatives of general formula (I):

in which $R_1$ to $R_5$ are as defined in the specification, to processes for preparing said derivatives, and to methods of use thereof.

7 Claims, No Drawings

OTHER PUBLICATIONS

Nicholson-Guthrie et al, Urine GABA Levels in Ovarian Cancer Patients: elevated GABA in malignancy, Cancer Letters, vol. 162, Issue 1, (2001), pp. 27-30.

Peterson et al, Integrating Pharmacology and in vivo Cancer Models in Preclinical and Clinical Drug Development, Eur J Cancer, 40 (2004) pp. 837-844.

Sausville et al, Contributions of Human Tumor Xenografts to Anticancer Drug Development, Cancer Res. 2006; 66(7), Apr. 1, 2006; pp. 3351-3354.

Abstract No. 1982-25808e (XP-002184731, DW 198213) (1982).

Derwent Patent Abstract No. 196800 (2003).

* cited by examiner

PYRIDOINDOLONE DERIVATIVES SUBSTITUTED IN THE 3-POSITION BY A HETEROCYCLIC GROUP, THEIR PREPARATION AND THEIR APPLICATION IN THERAPEUTICS

This application is a continuation of U.S. application Ser. No. 11/109,121, filed Apr. 19, 2005, now U.S. Pat. No. 7,456,193, which is a continuation of PCT International Application No. PCT/FR03/003111, filed Oct. 21, 2003, which are incorporated herein by reference in their entirety; which claims the benefit of priority of French Application No. 0213270, filed Oct. 23, 2002.

The present invention relates to pyridoindolone derivatives substituted in the 3-position by a heterocyclic group, to their preparation and to their application in therapeutics.

French Patent No. 97 08409 discloses compounds of formula:

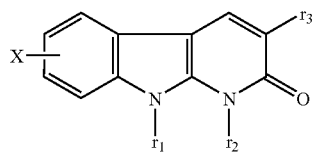

(A)

in which:
x represents a hydrogen or chlorine atom or a methyl or methoxy group;
$r_1$ represents a hydrogen atom or a methyl or ethyl group;
$r_2$ represents a methyl or ethyl group; or else
$r_1$ and $r_2$ together form a $(CH_2)_3$ group;
$r_3$ represents either, on the one hand, a phenyl group optionally substituted by a halogen atom or a methyl or methoxy group or, on the other hand, a thienyl group.

In the description of this patent, it is mentioned that the compounds of formula (A), which have an affinity for the omega modulatory sites associated with $GABA_A$ receptors, can be used in the treatment of conditions related to disorders of GABAergic transmission associated with $GABA_A$ receptor subtypes, such as anxiety, sleep disorders, epilepsy, and the like.

A subject-matter of the present invention is compounds having an anticancer activity corresponding to the formula:

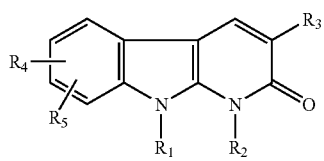

(I)

in which:
$R_1$ represents a hydrogen atom or a $(C_1-C_4)$alkyl group;
$R_2$ represents a hydrogen atom or a $(C_1-C_4)$alkyl group;
$R_3$ represents a thienyl mono- or polysubstituted by a methyl group; or a monocyclic or bicyclic heterocyclic radical chosen from: a pyridyl, an N-oxidopyridinio, a pyrazolyl, an (N-phenyl)pyrazolyl, an (N-halophenyl)pyrazolyl, a furyl, an indolyl, an (N-benzyl)indolyl, an (N-halobenzyl)indolyl, a benzothienyl or a benzofuryl, the said radicals being unsubstituted or substituted one or more times by a halogen atom or a methyl or methoxy group;
$R_4$ and $R_5$ are identical or different and each independently represent a hydrogen or halogen atom or a hydroxyl, hydroxymethyl, $(C_1-C_4)$alkyl, trifluoromethyl, $(C_1-C_4)$alkoxy, $(C_1-C_4)$alkoxycarbonyl or cyano group.

The compounds of formula (I) can exist in the form of bases or of addition salts with acids. Such addition salts form part of the invention.

These salts are advantageously prepared with pharmaceutically acceptable acids but the salts of other useful acids, for example for the purification or isolation of the compounds of formula (I), also form part of the invention.

The compounds of formula (I) can also exist in the form of hydrates or of solvates, namely in the form of associations or combinations with one or more water molecules or with a solvent. Such hydrates and solvates also form part of the invention.

In the context of the present invention:
a halogen atom is understood to mean: a fluorine, a chlorine, a bromine or an iodine;
a $(C_1-C_4)$alkyl group is understood to mean: a saturated, linear or branched, aliphatic group comprising 1 to 4 carbon atoms. Mention may be made, by way of example, of the methyl, ethyl, propyl, isopropyl, butyl, isobutyl and tert-butyl groups;
a $(C_1-C_4)$alkoxy group is understood to mean: an O-alkyl radical where the alkyl group is as defined above.

A subject-matter of the invention is very particularly compounds of formula (I) in which:
$R_1$ represents a hydrogen atom or a $(C_1-C_4)$alkyl group;
$R_2$ represents a hydrogen atom or a $(C_1-C_4)$alkyl group;
$R_3$ represents a thienyl mono- or polysubstituted by a methyl group; or a monocyclic or bicyclic heterocyclic radical chosen from: a pyridyl, a pyrazolyl, an (N-phenyl)pyrazolyl, an (N-halophenyl)pyrazolyl, a furyl, an indolyl, an (N-benzyl)indolyl, an (N-halobenzyl)indolyl, a benzothienyl or a benzofuryl, the said radicals being unsubstituted or substituted one or more times by a halogen atom or a methyl group;
$R_4$ and $R_5$ are identical or different and each independently represent a hydrogen or halogen atom or a hydroxyl, hydroxymethyl, $(C_1-C_4)$alkyl, trifluoromethyl, $(C_1-C_4)$alkoxy, $(C_1-C_4)$alkoxycarbonyl or cyano group.

Mention may be made, among the compounds of formula (I) which are subject-matters of the invention, of the preferred compounds which are defined as follows:
$R_1$ represents a hydrogen atom or a methyl group;
and/or $R_2$ represents a methyl group;
and/or $R_3$ represents a heterocyclic radical chosen from an N-oxidopyridinio, a pyridyl or a benzothienyl, the said radicals being unsubstituted or substituted one or more times by a halogen atom or a methyl or methoxy group;
and/or $R_4$ represents a methyl group;
and/or $R_5$ represents a hydrogen atom or a methyl group.

A particular subject-matter of the present invention is the following compounds:
1,6-dimethyl-3-(pyridin-4-yl)-1,9-dihydro-2H-pyrido[2,3-b]indol-2-one;
1,6,9-trimethyl-3-(pyridin-4-yl)-1,9-dihydro-2H-pyrido[2,3-b]indol-2-one;
1,6-dimethyl-3-(1-oxidopyridin-4-io)-1,9-dihydro-2H-pyrido[2,3-b]indol-2-one;
3-(4,6-dimethylpyridin-2-yl)-1,6-dimethyl-1,9-dihydro-2H-pyrido[2,3-b]indol-2-one;

3-(1-benzothien-5-yl)-1,6-dimethyl-1,9-dihydro-2H-pyrido[2,3-b]indol-2-one;

3-(5-chloro-1-benzothien-3-yl)-1,6,9-trimethyl-1,9-dihydro-2H-pyrido[2,3-b]indol-2-one;

3-(1H-indol-1-yl)-1,6-dimethyl-1,9-dihydro-2H-pyrido[2,3-b]indol-2-one;

3-(3-chloropyridin-4-yl)-1,6-dimethyl-1,9-dihydro-2H-pyrido[2,3-b]indol-2-one;

3-(2,6-dimethoxypyridin-4-yl)-1,6-dimethyl-1,9-dihydro-2H-pyrido[2,3-b]indol-2-one;

3-(2,6-dimethoxypyridin-4-yl)-1,6,9-trimethyl-1,9-dihydro-2H-pyrido[2,3-b]indol-2-one;

and their salts, hydrates and solvates.

In accordance with the invention, the compounds of general formula (I) can be prepared according to the following process.

This process is characterized in that:

a 2-aminoindole of formula:

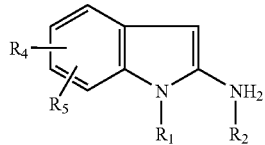

in which $R_1$, $R_2$, $R_4$ and $R_5$ are as defined for a compound of formula (I), is reacted with an ester of formula:

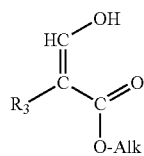

in which $R_3$ is as defined for a compound of formula (I) and Alk represents a $C_1$-$C_4$ alkyl.

The reaction is carried out in an aprotic, polar and preferably basic solvent, for example in pyridine, at a temperature of between ambient temperature and the reflux temperature of the solvent.

The aminoindoles of formula (II) can be prepared by methods such as those described in Khim. Geterosikl. Soedin., 1973, 12, 647-652 and in J. Heterocycl. Chem., 1975, 12, 135-138.

Some 2-aminoindole derivatives of formula (II) are known and are described in Khim. Geterosikl. Soedin., 1973, 4, 511-515; Eur. J. Med. Chem. Chim. Ther., 1992, 27 (9), 908-918; Chem. Heterocycl. Compd. (Engl. Transl.), 1970, 6, 338-343; Tetrahedron, 1971, 27, 775-785; Pharm. Chem. J. (Engl. Transl.), 1990, 24 (11), 810-812; Tetrahedron Lett., 1996, 37 (28), 4931-4932.

The esters of formula (III) can be prepared according to the following reaction scheme:

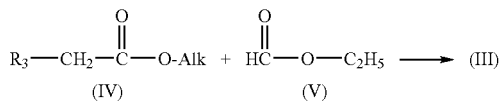

The acetic esters of formula (IV) or the corresponding acid derivatives are generally known and/or commercially available.

The methyl ester of 2-(4,5-dimethyl-2-thienyl)acetic acid is described in J. Heterocycl. Chem., 1988, 25, 1571-1581.

The compounds according to the invention can also be prepared by a process characterized in that:

an aminoindole of formula:

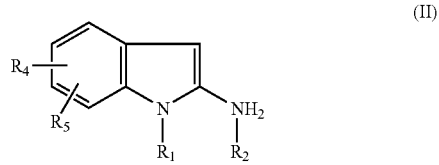

in which $R_1$, $R_2$, $R_4$ and $R_5$ are as defined for a compound of formula (I), is reacted with an ester of formula:

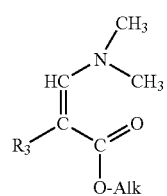

in which $R_3$ is as defined for a compound of formula (I) and Alk represents a $C_1$-$C_4$ alkyl.

The reaction is carried out in a protic and polar solvent, preferably in an acidic medium, at a temperature of between ambient temperature and the reflux temperature of the solvent.

The compound of formula (VI) is prepared using dimethoxy-N,N-dimethylmethanamine (VII) by a method similar to that described in J. Org. Chem., 1982, 47, 2846-2851 or using Bredereck's reagent (tert-butoxybis(dimethylamino)methane) according to J. Org. Chem., 1982, 15, 2846-2851 and according to the following reaction scheme:

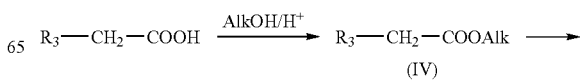

-continued $$\underset{(VI)}{\overset{\displaystyle R_3}{\underset{\displaystyle}{\bigg|}}}\begin{array}{c}CH_3\\N\\HC\diagdown N\diagdown CH_3\\\|\\C\\\diagdown C\diagup^O\\O\text{-Alk}\end{array}$$

The preparation of some compounds in accordance with the invention is described in the following examples. These examples are not limiting and serve only to illustrate the present invention. The numbers of the compounds in the examples refer to those given in the table below, in which the chemical structures and the physical properties of a few compounds according to the invention are illustrated.

The signals observed by proton nuclear magnetic resonance (NMR) are recorded in $d_6$-DMSO optionally comprising TFA; the reference is placed in the $d_6$-DMSO, which lies at 2.50 ppm from the tetramethylsilane. The chemical shifts δ are expressed in ppm and the signals are expressed thus: s: singlet; bs: broad singlet; d: doublet; sd: split doublet; t: triplet; st: split triplet; q: quartet; mt: multiplet.

In the preparations and examples which will follow, the following abbreviations are used:

TFA: trifluoroacetic acid
DMSO: dimethyl sulphoxide
DCM: dichloromethane
DMF: dimethylformamide
AcOEt: ethyl acetate
AcOH: acetic acid
MTBE: methyl tert-butyl ether
AT: ambient temperature
TLC: thin layer chromatography.

Preparation of the Compounds of Formula (II)

The compounds of formula (II) can exist in two tautomeric forms:

Preparation 1.1

N,1,5-Trimethyl-1H-indol-2-amine hydrochloride

A) N'-(4-Methylphenyl)acetohydrazide 104.8 g of 1-(4-methylphenyl)hydrazine hydrochloride are suspended in 525 ml of isopropyl acetate, a solution of 104.8 g of potassium carbonate in 300 ml of water is added and then the mixture is stirred until the solid has disappeared. 77.4 g of acetic anhydride are added while maintaining the temperature below 20° C. and then the mixture is left stirring at 20° C. A precipitate is observed to form, which precipitate disappears when the mixture is heated at approximately 55-60° C. The organic phase is washed twice with 200 ml of water and is then cooled at 0-5° C. overnight. The product formed is recovered by filtration and is then washed twice with 100 ml of MTBE.

NMR CDCl$_3$ (300 MHz): 2.02 ppm: s: 3H, 2.29 ppm: s: 3H, 6.14 ppm: d: 1H, 6.73 ppm: d: 2H, 7.03 ppm: d: 2H, 7.72 ppm 1H.

B) N,N'-Dimethyl-N'-(4-methylphenyl)acetohydrazine 60 g of hydrazine from the preceding stage and 11.8 g of tetrabutylammonium bromide are suspended in 240 ml of toluene, and 292 g of 50% NaOH in water and then 155.6 g of methyl iodide are added. 83 g of sodium hydroxide pellets are then added and then the reaction medium is heated at 80° C. for 6 hours. The mixture is cooled to 30-35° C. and then 500 ml of water are added. The organic phase is washed three times with 100 ml of water. The organic phase is dried by azeotropic distillation of the water under reduced pressure.

NMR CDCl$_3$ (300 MHz): 2.15 ppm: s: 3H, 2.31 ppm: s: 3H, 2.95 ppm: s: 3H, 3.10 ppm: s: 3H, 6.63 ppm: d: 2H, 7.13 ppm d: 2H.

C) N,1,5-Trimethyl-1H-indol-2-amine hydrochloride

The product obtained in the preceding stage is dissolved in toluene, 61.5 g of phosphorus oxychloride are added and the mixture is heated at 80° C. for 2 hours. 100 ml of ethyl acetate are added at 80° C. and then the medium is cooled to AT. The precipitate is filtered off and then washed twice with 50 ml of ethyl acetate, m.p.=222° C.

NMR $d_6$-DMSO (200 MHz): 2.36 ppm: s: 3H, 3.11 ppm: s: 3H, 3.49 ppm: s: 3H, 4.29 ppm: s: 1H, 7.25-7.35 ppm: unresolved peak: 3H, 10.07 ppm: unresolved peak: 1H.

Preparation 1.2

N,5-Dimethyl-1H-indol-2-amine dihydrochloride

A) N'-(4-Methylphenyl)acetohydrazide

Another process for the preparation of this compound is described below.

5 g of 1-(4-methylphenyl)hydrazine hydrochloride are dissolved in water and then triethylamine is added until the salt has been neutralized. Extraction is carried out with AcOEt and then the extract is evaporated to dryness. The precipitate formed is dissolved in 30 ml of ether and then a solution of 4.6 ml of acetic anhydride dissolved in 30 ml of ether is added dropwise. The mixture is stirred at 0° C. for 15 minutes and then the precipitate formed is filtered off to produce 3 g of the expected compound.

NMR CDCl$_3$ (300 MHz): 2.02 ppm: s: 3H, 2.29 ppm: s: 3H, 6.14 ppm: d: 1H, 6.73 ppm: d: 2H, 7.03 ppm: d: 2H, 7.72 ppm 1H.

B) N-Methyl-N'-(4-methylphenyl)acetohydrazide 0.8 g of 60% NaH is suspended in 30 ml of DMF. 3.2 g of hydrazine obtained in the preceding stage in 20 ml of DMF are added dropwise at 0° C. When gas evolution has ceased, 1.8 ml of methyl iodide are added and the mixture is stirred at AT for one hour. The mixture is poured onto a saturated NH$_4$Cl solution and then extraction is carried out with AcOEt. Washing is carried out several times with a saturated NaCl solution and then evaporation is carried out to dryness. The residue is purified by chromatography on a silica column eluted with an AcOEt/heptane mixture, (25/75; v/v) then (50/50; v/v), to produce 1.0 g of the expected compound in the form of a white powder.

NMR CDCl$_3$ (200 MHz): 2.21 ppm: s: 3H, 2.32 ppm: s: 3H, 3.15 ppm: s: 3H, 5.88 ppm: s: 1H, 6.64 ppm: d: 2H, 7.12 ppm d: 2H.

C) N,5-Dimethyl-1H-indol-2-amine dihydrochloride 1.0 g of the compound from the preceding stage is dissolved in 20 ml of POCl$_3$ and then the mixture is heated at 100° C. for two hours. The reaction mixture is cooled and then ether is added. The precipitate formed is filtered off and is washed with ether to produce 1.3 g of the expected compound.

NMR d$_6$-DMSO (300 MHz): 2.31 ppm: s: 3H, 3.05 ppm: s: 3H, 4.14 ppm: s: 2H, 7.07-7.23 ppm: unresolved peak: 3H, 10.51 ppm: s: 1H, 12.37 ppm: d: 1H.

Preparation of the Intermediates of Formulae (III) and (VI)

The compounds (III) can exist in 2 tautomeric forms:

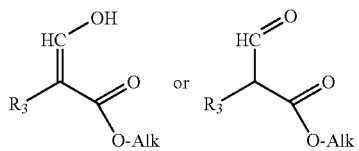

Preparation 2.1

Methyl 3-(dimethylamino)-2-(2-pyridinyl)-2-propenoate (VI)

10 g of ethyl 2-(2-pyridinyl)acetate, 39 ml of dimethoxy-N,N-dimethylmethanamine and 1.5 ml of N,N,N',N'-tetramethylenediamine are mixed and the mixture is heated at 130° C. for 18 hours. The mixture is taken up in 120 ml of a mixture of equal volumes of AcOEt and of a saturated NH$_4$Cl solution. The organic phase is separated by settling, washed with a saturated NaCl solution, dried over Na$_2$SO$_4$ and evaporated to produce the expected product in the form of an oil.

NMR (250 MHz d$_6$-DMSO): 1.1 ppm: t: 3H, 2.6 ppm: s: 6H; 4 ppm: q: 2H, 7.1-7.3 ppm: unresolved peak: 2H, 7.5 ppm: s: 1H, 7.6 ppm: mt: 1H, 8.5 ppm: d: 1H.

Preparation 2.2

Methyl 3-hydroxy-2-(4-pyridinyl)propenoate (III)

9 g of ethyl 2-(4-pyridinyl)acetate and 1.35 g of 95% NaH are mixed in 90 ml of toluene. The mixture is heated at 100° C. for 30 minutes and is then cooled, and 8.8 ml of ethyl formate are added. The mixture is left stirring at AT for 1 hour and at 100° C. for 45 minutes. The reaction medium is cooled and then 25.5 ml of 2N HCl are added. Filtration is carried out and then the precipitate formed is taken up in AcOEt and then in ether to produce 5.65 g of the expected compound.

NMR (200 MHz d$_6$-DMSO): 1.1 ppm: t: 3H; 4 ppm: q: 2H; 8 ppm: d: 2H, 8.6 ppm: d: 2H, 9.7 ppm: s: 1H.

The intermediates collated in the table below were prepared by following the procedure as described in Preparation 2.1: (Me represents methyl)

TABLE 1

(VI)

| Preparation | R$_3$ | Alk | Characterization M.p. (° C.) and/or NMR |
|---|---|---|---|
| 2.3 | 4-methyl-3-methyl-1-phenyl-pyrazol-5-yl | Me | (d$_6$-DMSO 200 MHz): 2.2 ppm: s: 3H; 2.8 ppm: s: 6H; 3.6 ppm: s: 3H; 7.5-7.7 ppm: unresolved peak: 6H. |
| 2.4 | 1-methyl-3-methyl-indol-2-yl | Me | 156° C. |
| 2.5 | 1-(4-fluorobenzyl)-3-methyl-indol-2-yl | Me | 119° C. |

TABLE 1-continued

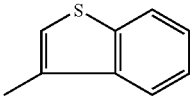
(VI)

| Preparation | R₃ | Alk | Characterization M.p. (° C.) and/or NMR |
|---|---|---|---|
| 2.6 | 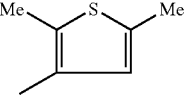 | Me | 128° C. |
| 2.7 | 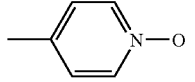 | Me | 75° C. |
| 2.8 | 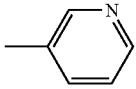 | Et | (d₆-DMSO 200 MHz): 1.1 ppm: t: 3H; 2.7 ppm: s: 6H; 3.95 ppm: q: 2H; 7.05 ppm: d: 2H; 7.55 ppm: s: 1H; 8 ppm: d: 2H. (a) |
| 2.9 | 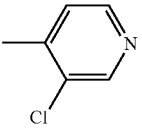 | Et | (d₆-DMSO/TFA 200 MHz): 1.05 ppm: t: 3H; 2.65 ppm: s: 6H; 4 ppm: q: 2H; 7.25-7.35 ppm: unresolved peak: 1H; 7.5-7.6 ppm: unresolved peak: 1H; 7.65 ppm: s: 1H; 8.3 ppm: d: 1H; 8.4: d: 1H. |
| 2.10 | 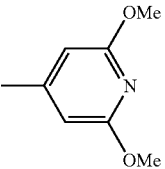 | Me | (d₆-DMSO/TFA 200 MHz): 2.8 ppm: s: 6H; 3.6 ppm: s: 3H; 7.35 ppm: d: 1H; 7.7 ppm: s: 1H; 8.4 ppm: d: 1H; 8.6 ppm: s: 1H. (b) |
| 2.11 | 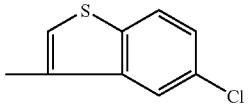 | Me | (d₆-DMSO/TFA 200 MHz): 2.7 ppm: s: 6H; 3.5 ppm: s: 3H; 3.85 ppm: s: 6H; 6.1 ppm : s : 2H; 7.5 ppm: s: 1H. (c) |
| 2.12 | 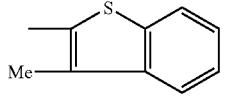 | Me | (d₆-DMSO/TFA 200 MHz): 2.6 ppm: s: 6H; 3.45 ppm: s: 3H; 7.35 ppm: d: 1H; 7.4 ppm: s: 1H; 7.5 ppm: s: 1H; 7.7 ppm: s: 1H; 8 ppm: d: 1H. |
| 2.13 | 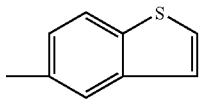 | Me | 142° C. |
| 2.14 |  | Me | (d₆-DMSO/TFA 200 MHz): 3.65 ppm: s: 6H; 3.75 ppm: s: 3H; 7.15 ppm: d: 1H; 7.4 ppm: d: 1H; 7.6 ppm: s: 1H; 7.65 ppm: d: 1H; 7.75 ppm: d: 1H; 7.90 ppm: d: 1H. |

TABLE 1-continued

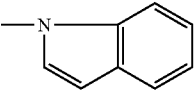

| Preparation | $R_3$ | Alk | Characterization M.p. (° C.) and/or NMR |
|---|---|---|---|
| 2.15 | indol-1-yl | Et | ($d_6$-DMSO/TFA 200 MHz): 1.05 ppm: t: 3H; 2.5 ppm: s: 6H; 4 ppm: q: 2H; 6.45 ppm: d: 1H; 7-7.2 ppm: unresolved peak: 4H; 7.55 ppm: d: 1H; 7.7 ppm: s: 1H. |

(a): The intermediate 2.8 is prepared from ethyl (1-oxidopyridin-4-io)acetate by the action of Bredereck reagent by heating at 85° C. for 2 and a half hours.

(b): The compound of Preparation 2.10 is obtained by the action of Bredereck reagent on methyl (3-chloropyridin-4-yl) acetate, itself prepared as follows. 13.25 ml of diisopropylamine and 58.79 ml of 1.6M BuLi in hexane are added at −78° C. to 160 ml of THF and then 10 g of 3-chloro-4-methylpyridine (prepared according to J. Organomet. Chem., FR, 1981, 216 (2), 139-147) in 10 ml of THF are added. The mixture is left stirring at 50° C. for 30 minutes, then 12.11 ml of dimethyl carbonate are added and the mixture is stirred at 50° C. for 30 minutes and then at AT for 18 hours. 100 ml of ethyl acetate are added and then extraction is carried out with 100 ml of ethyl acetate (3 times). The organic phase is dried over $MgSO_4$ and evaporated and then the residue is chromatographed on silica to produce 310 mg of the expected compound.

NMR $d_6$-DMSO/TFA (200 MHz): 3.6 ppm: unresolved peak 3H, 3.85 ppm: s: 2H, 7.45 ppm: d: 1H, 8.4 ppm: d: 1H, 8.6 ppm: s: 1H.

(c): The compound of Preparation 2.11 is prepared by the action of Bredereck reagent on methyl (2,6-dimethoxypyridin-4-yl)acetate. This compound is prepared according to the following stages.

A) 4-Bromomethyl-2,6-dimethoxypyridine 1 g of (2,6-dimethoxypyridin-4-yl)methanol, prepared according to J. Heterocl. Chem., 1974, 11, 251, is dissolved in 20 ml of $CH_2Cl_2$, 0.84 ml of $PBr_3$ is added and then the mixture is left stirring at AT for 10 hours. Pentane is added and the precipitate formed is filtered off, washed with pentane and then dried to produce 850 mg of the expected compound.

NMR $d_6$-DMSO (200 MHz): 3.75 ppm: s: 6H, 4.45 ppm 2H, 6.35 ppm: s: 2H.

B) 4-Cyanomethyl-2,6-dimethoxypyridine 4.3 g of the compound from the preceding stage are mixed with 40 ml of EtOH and 2.33 g of KCN, the mixture is heated at reflux for 2 hours and then the solvent is evaporated. The residue is taken up in $CH_2Cl_2$ and then the organic phase is washed with water, dried and evaporated. The solid obtained is washed with pentane and 1.8 g of the expected compound are obtained.

NMR $d_6$-DMSO (200 MHz): 3.9 ppm: s: 6H, 4.1 ppm: s 2H, 6.4 ppm: s: 2H.

C) 2,6-Dimethoxypyridine-4-acetic acid 1.62 g of the compound from the preceding stage are placed in 50 ml of EtOH, 2.96 ml of 10N NaOH are added and then the mixture is heated at reflux for 3 hours. It is evaporated to dryness, the residue is taken up in the minimum amount of water and then the pH is brought to 6 by addition of concentrated HCl. Extraction is carried out with AcOEt and the organic phase is dried and evaporated to produce 1.5 g of the expected compound.

NMR $d_6$-DMSO (200 MHz): 3.5 ppm: s: 2H, 3.8 ppm: s 6H, 6.25 ppm: s: 2H, 12.50 ppm: bs: 1H.

D) Methyl (2,6-dimethoxypyridin-4-yl)acetate 1.7 g of the compound from the preceding stage are placed in 15 ml of MeOH, cooling is carried out to +4° C. and then 2.5 ml of thionyl chloride are added dropwise. The mixture is left stirring at AT for 1 hour and is evaporated to dryness, and the residue is taken up in MeOH and then again evaporated and dried to produce 1 g of the expected compound.

The following intermediate was prepared by following the procedure as described in Preparation 2.2.

Preparation 2.16

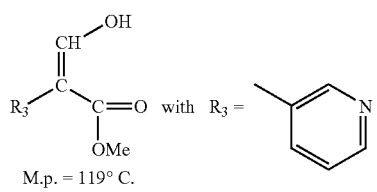

M.p. = 119° C.

EXAMPLE 1

Compound 3

1,6,9-Trimethyl-3-(2-pyridinyl)-1,9-dihydro-2H-pyrido[2,3-b]indol-2-one hydrochloride 1 g of the compound from Preparation 1.1 and 1.25 g of the compound from Preparation 2.1 are mixed in 5 ml of AcOH and the mixture is heated at 100° C. for 18 hours. The reaction medium is poured into 80 ml of water and the pH is brought to 9 by addition of a concentrated NaOH solution. The gum obtained is dissolved in 30 ml of a mixture AcOEt and DCM (1/1; v/v) and then washing is carried out with a saturated NaCl solution. The organic phase is dried over $Na_2SO_4$ and evaporated to produce a yellow oil which is taken up in ethereal hydrochloric acid. The precipitate formed is filtered off and dried to give 200 mg of the expected compound in the form of a yellow powder, M.p. >260° C.

NMR (200 MHz $d_6$-DMSO/TFA): 2.2 ppm: s: 3H, 3.9 ppm 6H, 7.1 ppm: d: 1H, 7.2 ppm: d: 1H, 7.6 ppm: unresolved peak: 2H, 8.2-8.5 ppm: unresolved peak: 3H, 8.9 ppm: s: 1H.

EXAMPLE 2

Compound 2

1,6,9-Trimethyl-3-(4-pyridinyl)-1,9-dihydro-2H-pyrido[2,3-b]indol-2-one hydrochloride 1 g of the compound from Preparation 1.1 and 0.744 g of the compound from Preparation 2.2 are mixed in 10 ml of pyridine. The mixture is heated at 100° C. until the compound from Preparation 2.2 has disappeared by TLC, then the pyridine is evaporated and the residue is taken up in an AcOEt/$H_2O$ (1/1; v/v) mixture. The organic phase is dried over $Na_2SO_4$ and then evaporated; the residue is taken up in AcOEt and a precipitate is formed by addition of ethereal hydrochloric acid. The precipitate is filtered off and dried to give 180 mg of the expected compound in the form of a yellow powder, M.p. >250° C.

NMR (200 MHz $d_6$-DMSO): 2.6 ppm: s: 3H; 4 ppm: s 3H, 4.1 ppm: s: 3H, 7.2 ppm: d: 1H, 7.5 ppm: d: 1H, 7.9 ppm: s: 1H, 8.8 ppm: s: 4H, 9.2 ppm: s: 1H.

EXAMPLE 3

Compound 4

1,6-Dimethyl-3-(pyridin-4-yl)-1,9-dihydro-2H-pyrido[2,3-b]indol-2-one hydrochloride 1.5 of the compound from Preparation 1.2 and 2 g of the compound from Preparation 2.2 are dissolved in 20 ml of AcOH. The mixture is heated at 100° C. for 18 hours and then the reaction medium is poured into 100 ml of water. Extraction is carried out with $Et_2O$ and then the aqueous phase is brought to pH=10 by addition of concentrated NaOH. Extraction is carried out several times with an AcOEt/$CH_2Cl_2$ (1/1; v/v) mixture. The organic phase is washed with water, dried and then evaporated. The residue is dissolved in a minimum amount of MeOH and is then precipitated with ethereal hydrochloric acid. The precipitate is filtered off, washed with $Et_2O$ and then dried to produce 0.680 g of the expected compound.

EXAMPLE 4

Compound 10

3-(1-Benzothien-3-yl)-1,6-dimethyl-1,9-dihydro-2H-pyrido[2,3-b]indol-2-one 2 g of the compound from Preparation 1.2 are dissolved in 10 ml of AcOH, the solution is heated to 100° C., then 2.66 g of the compound from Preparation 2.6 in 10 ml of AcOH are added and the mixture is heated at 100° C. for 2 hours. Cooling is carried out and then the precipitate is filtered off, subsequently washed twice with $Et_2O$ and then dried to give 2.47 g of the expected compound.

EXAMPLE 5

Compound 9

3-(1-Benzothien-3-yl)-1,6,9-trimethyl-1,9-dihydro-2H-pyrido[2,3-b]indol-2-one 2.46 g of the compound from the preceding example are dissolved in 25 ml of DMSO, 2.7 g of $K_2CO_3$ and 5 ml of methyl iodide are added and then the mixture is left stirring at 40° C. for 18 hours. The reaction medium is filtered and then the filtrate is poured into 300 ml of water. Filtering is again carried out and the solid is washed 3 times with water. Drying is carried out, washing is carried out 3 times with ether and drying is again carried out to produce 2.44 g of the expected compound.

EXAMPLE 6

Compound 13

1,6,9-Trimethyl-3-(1-oxidopyridin-4-io)-2,9-dihydro-1H-pyrido[2,3-b]indol-2-one 300 mg of Compound 2 and 30 ml of MeOH are mixed, then 373 mg of m-chloroperbenzoic acid in 5 ml of $CH_2Cl_2$ are added at 0° C. and the mixture is stirred at AT for 3 hours. It is evaporated and the residue is taken up in a sodium bisulphite solution and then extracted with $CH_2Cl_2$. The organic phase is dried and evaporated, the residue is then taken up in $Et_2O$, filtration is carried out and drying is again carried out to produce 235 mg of the expected compound.

The physical properties of a few compounds according to the invention are illustrated in the following table. In this table, Me represents methyl.

TABLE 2

(I)

| Compound | $R_1$ | $R_3$ | Characterization M.p. (° C.) or NMR |
|---|---|---|---|
| 1 | Me | 3-pyridyl | M.p. > 250° C. (200 MHz, $d_6$-DMSO/TFA): 2.4 ppm: s: 3H; 4 ppm: s: 3H; 4.1 ppm: s: 3H; 7.1 ppm: d: 1H; 7.5 ppm: d: 1H; 7.7 ppm: s: 1H; 8 ppm: unresolved peak: 1H; 8.8 ppm: d: 1H; 8.9 ppm: s: 1H; 9 ppm: d: 1H; 9.4 ppm: s: 1H. |

TABLE 2-continued

Structure (I): tricyclic scaffold with Me substituent on benzene ring, R₁ on indole N, N-Me on lactam nitrogen, and R₃ at position 3 of the pyridinone ring.

| Compound | R₁ | R₃ | Characterization M.p. (° C.) or NMR |
|---|---|---|---|
| 2 | Me | 4-pyridyl | M.p. > 250° C. (200 MHz, d₆-DMSO): 2.6 ppm: s: 3H; 4 ppm: s: 3H; 4.1 ppm: s: 3H; 7.2 ppm: d: 1H: 7.5 ppm: d: 1H; 7.9 ppm: s: 1H; 8.8 ppm: s: 4H; 9.2 ppm : s: 1H. |
| 3 | Me | 2-pyridyl | M.p. > 260° C. (200 MHz, d₆-DMSO/TFA): 2.2 ppm: s: 3H; 3.9 ppm: s: 6H; 7.1 ppm: d: 1H; 7.2 ppm: d: 1H; 7.6 ppm: unresolved peak: 2H; 8.2-8.5 ppm : unresolved peak: 3H; 8.9 ppm: s: 1H. |
| 4 | H | 4-pyridyl | M.p. > 280° C. (200 MHz, d₆-DMSO/TFA): 2.3 ppm: s: 3H; 3.6 ppm: s: 3H; 7.1 ppm: d: 1H; 7.4 ppm: d: 1H; 7.8 ppm: s: 1H; 8.5-8.7 ppm: unresolved peak: 4H; 9 ppm: s: 1H. |
| 5 | Me | 1-methyl-1H-indol-3-yl | M.p. = 236° C. |
| 6 | H | 2-pyridyl | M.p. > 270° C. (200 MHz, d₆-DMSO): 2.3 ppm: s: 3H; 3.6 ppm: s: 3H; 7 ppm: d: 1H; 7.1 ppm: unresolved peak: 1H; 7.2 ppm: d: 1H; 7.7 ppm: unresolved peak: 2H; 8.5 ppm: unresolved peak: 2H, 9 ppm: s: 1H; 11.9 ppm: s: 1H. |
| 7 | Me | 1-(4,5-dimethyl-pyrazolyl)phenyl | M.p. = 130° C. |
| 8 | Me | 1-(4-fluorobenzyl)-1H-indol-3-yl | M.p. = 115° C. |
| 9 | Me | benzothiophen-3-yl | M.p. = 220° C. |
| 10 | H | benzothiophen-3-yl | M.p. = 280° C. |

TABLE 2-continued (I)

| Compound | R₁ | R₃ | Characterization M.p. (° C.) or NMR |
|---|---|---|---|
| 11 | Me | 3,4-dimethyl-2,5-dimethylthiophene (Me, S, Me with Me) | M.p. = 218° C. |
| 12 | H | 3,4-dimethyl-2,5-dimethylthiophene (Me, S, Me with Me) | M.p. > 280° C. (200 MHz, $d_6$-DMSO): 2.2 ppm: ss: 3H; 2.35 ppm: s: 3H; 3.6 ppm: s: 3H; 6.7 ppm: s: 1H; 7 ppm: d: 1H; 7.3 ppm: d: 1H; 7.6 ppm: s: 1H; 8 ppm: s: 1H; 11.8 ppm: s: 1H. |
| 13 | Me | pyridine N-oxide | (200 MHz, $d_6$-DMSO/TFA): 2.4 ppm: s: 3H; 3.9 ppm: s: 3H; 4 ppm: s: 3H; 7.1 ppm: d: 1H; 7.4 ppm: d: 1H; 7.7 ppm: s: 1H; 8.25 ppm: d: 2H; 8.5 ppm: d: 2H; 8.8 ppm: s: 1H |
| 14 | H | pyridine N-oxide | (200 MHz, $d_6$-DMSO/TFA): 2.5 ppm: s: 3H; 3.75 ppm: s: 3H; 7.15 ppm: d: 1H; 7.4 ppm: d: 1H; 7.8 ppm: s: 1H; 8.2 ppm: d: 1H; 8.4 ppm: d: 1H; 8.8 ppm: s: 1H |
| 15 | H | 2,6-dimethylpyridine with Me | (200 MHz, $d_6$-DMSO/TFA): 2.25 ppm: s: 3H; 2.5 ppm: s: 3H; 2.55 ppm: s: 3H; 3.75 ppm: s: 3H; 6.9 ppm: s: 1H; 7.1 ppm: d: 1H; 7.4 ppm: d: 1H; 7.7 ppm: s: 1H; 8.25 ppm: s: 1H; 9.05 ppm: s: 1H |
| 16 | H | 3-pyridyl | (200 MHz, $d_6$-DMSO/TFA): 2.4 ppm: s: 3H; 3.65 ppm: s: 3H; 7 ppm: d: 1H; 7.25-7.4 ppm: unresolved peak: 2H; 7.65 ppm: s: 1H; 8.15 ppm: sd: 1H; 8.4 ppm: d: 1H; 8.45 ppm: s: 1H; 8.9 ppm: s: 1H |
| 17 | H | 3-chloro-4-methylpyridine | (200 MHz, $d_6$-DMSO/TFA): 2.4 ppm: s: 3H; 3.7 ppm: s: 3H; 7.1 ppm: d: 1H; 7.45 ppm: d: 1H; 7.55 ppm: d: 1H; 7.7 ppm: s: 1H; 8.3 ppm: s: 1H; 8.55 ppm: d: 1H; 8.75 ppm: s: 1H |
| 18 | H | 2,6-dimethoxy-4-pyridyl | (200 MHz, $d_6$-DMSO/TFA): 2.45 ppm: s: 3H; 3.7 ppm: s: 3H; 3.95 ppm: s: 6H; 7 ppm: s: 2H; 7.15 ppm: d: 1H; 7.4 ppm: d: 1H; 7.8 ppm: s: 1H; 8.65 ppm: s: 1H |

TABLE 2-continued

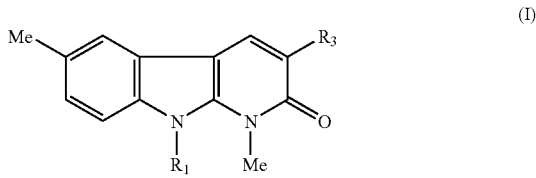

(I)

| Compound | $R_1$ | $R_3$ | Characterization M.p. (° C.) or NMR |
|---|---|---|---|
| 19 | Me | 2,6-dimethoxy-4-methylpyridin-3-yl | (200 MHz, $d_6$-DMSO/TFA): 2.4 ppm: s: 3H; 3.8 ppm: s: 6H; 4 ppm: s: 3H; 4.1 ppm: s: 3H; 6.95 ppm: s: 2H; 7.1 ppm: d: 1H; 7.5 ppm: d: 1H; 7.8 ppm: s: 1H; 8.6 ppm: s: 1H |
| 20 | H | 5-chlorobenzothiophen-3-yl | (200 MHz, $d_6$-DMSO/TFA): 2.4 ppm: s: 3H; 3.65 ppm: s: 3H; 7 ppm: d: 1H; 7.25-7.4 ppm: unresolved peak: 2H; 7.55 ppm: d: 1H; 7.6 ppm: d: 1H; 7.8 ppm: s: 1H; 8.05 ppm: d: 1H; 8.25 ppm: s: 1H |
| 21 | Me | 5-chlorobenzothiophen-3-yl | (200 MHz, $d_6$-DMSO/TFA): 2.4 ppm: s: 3H; 4 ppm: s: 3H; 4.15 ppm: s: 3H; 7.1 ppm: d: 1H; 7.3-7.5 ppm: unresolved peak: 2H; 7.55 ppm: d: 1H; 7.7 ppm: d: 1H; 7.8 ppm: s: 1H; 8.05 ppm: d: 1H; 8.3 ppm: d: 1H |
| 22 | H | 2,3-dimethylbenzothiophen-?-yl | (200 MHz, $d_6$-DMSO/TFA): 2.25 ppm: s: 3H; 2.3 ppm: s: 3H; 3.65 ppm: s: 3H; 7 ppm: d: 1H; 7.2-7.4 ppm: unresolved peak: 3H, 7.65 ppm: s: 1H, 7.75 ppm: d: 1H; 7.85 ppm: d: 1H; 8.25 ppm: s: 1H |
| 23 | Me | 2,3-dimethylbenzothiophen-?-yl | 245° C. |
| 24 | H | benzothiophen-2-yl | (200 MHz, $d_6$-DMSO/TFA): 2.4 ppm: s: 3H; 3.7 ppm: s: 3H; 7.05 ppm: d: 1H; 7.4 ppm: d: 1H; 7.5 ppm: d: 1H; 7.75 ppm: unresolved peak: 2H; 7.8 ppm: d: 1H; 8 ppm: d: 1H; 8.3 ppm: d: 1H; 8.45 ppm: s: 1H |
| 25 | Me | benzothiophen-2-yl | (200 MHz, $d_6$-DMSO/TFA): 2.45 ppm: s: 3H; 4.05 ppm: s: 3H; 4.15 ppm: s: 3H; 7.2 ppm: d: 1H; 7.55 ppm: d: 1H; 7.6 ppm: s: 1H; 7.85 ppm: d: 2H; 7.9 ppm: s: 1H; 8.1 ppm: d: 1H; 8.4 ppm: s: 1H; 8.5 ppm: s: 1H. |
| 26 | H | indol-1-yl | (200 MHz, $d_6$-DMSO/TFA): 2.4 ppm: s: 3H; 3.75 ppm: s: 3H; 6.6 ppm: d: 1H; 7-7.25 ppm: unresolved peak: 4H; 7.4 ppm: s: 1H; 7.45 ppm: d: 1H; 7.65 ppm: d: 1H; 7.7 ppm: d: 1H; 8.4 ppm: s: 1H. |

TABLE 2-continued

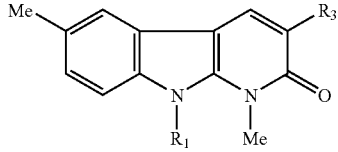

(I)

| Compound | $R_1$ | $R_3$ | Characterization M.p. (° C.) or NMR |
|---|---|---|---|
| 27 | Me | (indole structure) | (200 MHz, $d_6$-DMSO/TFA): 2.5 ppm: s: 3H; 4.1 ppm: s: 3H; 4.2 ppm: s: 3H; 6.6 ppm: d: 1H; 7-7.25 ppm: unresolved peak: 4H; 7.45 ppm: d: 1H; 7.55 ppm: d: 1H; 7.65 ppm: d: 1H; 7.75 ppm: s: 1H. |

The compounds of formula (I) according to the present invention were tested in vitro on a human breast cancer cell line: the MDA-MB-231 line available from the American Type Culture Collection (reference HTB26).

The antiproliferative effect is evaluated according to J. M. Derocq et al., FEBS Letters, 1998, 425, 419-425: the level of incorporation of [3H]thymidine in the DNA of the treated cells is measured after incubating a compound of formula (I) for 96 hours. The inhibitory concentration 50 ($IC_{50}$) is defined as the concentration which inhibits cell proliferation by 50%.

The compounds according to the invention exhibit an $IC_{50}$ generally of less than 10 μM with regard to the MDA-MB-231 line.

The compounds of formula (I) were also tested on another human breast cancer cell line, a "multi-drug-resistant" (MDR) line referred to as MDA-$A_1$. This line is described by E. Collomb, C. Dussert and P. M. Martin in Cytometry, 1991, 12(1), 15-25.

The term "multi-resistant" which describes this line means that the said line is generally not very sensitive to the chemotherapeutic drugs commonly used and in particular to antimitotics of natural origin, such as paclitaxel, vincristine or vinblastine.

The compounds according to the invention exhibit an $IC_{50}$ generally of less than 10 μM with regard to the MDA-$A_1$ multi-resistant line.

The compounds according to the invention were also tested in vivo in murine models of human tumour xenografts according to the methods described in the literature: Mooberry S. L. et al., Int. J. Cancer, 2003, 104 (4), 512-521; Polin L. et al., Invest. New Drugs, 2002, 20 (1), 13-22; Corbett T. H et al., Invest. New Drugs, 1999, 17 (1), 17-27. Fragments of human tumours with a diameter of 2 to 3 mm are implanted subcutaneously in SCID (Severe Combined Immunodeficiency) mice of the Balb/C strain (Iffa-Credo, Lyons, France). When these tumours reach a weight of 50-60 mg, the compounds are administered orally or intravenously every day or every two days throughout the duration of the experiment (20 to 40 days) at doses varying from 10 to 300 mg/kg per administration. The weight of the tumours is estimated according to the formula: W (weight of the tumour in mg)=(a×$b^2$)/2, where a and b respectively represent the length and the width in mm of the tumour implant. The measurement of a and of b is carried out using a calliper rule. The antitumour effectiveness is evaluated by comparing the mean weight of the tumours in the group of animals treated with the test compound (T) with that of the animals of the control group to which only the solvent of the compound has been administered (C). This measurement, expressed as % of the ratio T/C, is carried out when C reaches approximately 1 000 mg. The compounds according to the invention demonstrated an in vivo antitumour activity (ratio T/C of less than 100%), some very significantly with a ratio T/C of less than or equal to 42%.

Thus, according to the present invention, it is apparent that the compounds of formula (I) inhibit the proliferation of tumour cells, including those of cells exhibiting multi-resistance. It is thus apparent that the compounds according to the invention have an anticancer activity.

Thus, according to another of its aspects, a subject-matter of the invention is medicaments which comprise a compound of formula (I) or an addition salt of the latter with a pharmaceutically acceptable acid or also a hydrate or a solvate of the compound of formula (I).

These medicaments find their use in therapeutics, in particular in the treatment of or protection from diseases caused or exacerbated by the proliferation of tumour cells.

These compounds, as inhibitor of the proliferation of tumour cells, are of use in the treatment of solid tumours, both primary and metastatic solid tumours, carcinomas and cancers, in particular: breast cancer; lung cancer; cancer of the small intestine, cancer of the colon and of the rectum; cancer of the respiratory tract, of the oropharynx and of the hypopharynx; cancer of the oesophagus; liver cancer, stomach cancer, cancer of the bile ducts, cancer of the gall bladder, cancer of the pancreas; cancers of the urinary tract, including kidney, urothelium and bladder; cancers of the female genital tract, including cancer of the uterus, cervix and ovaries, choriocarcinoma and trophoblastic cancer; cancers of the male genital tract, including cancer of the prostate, seminal vesicles and testicles, tumours of the germinal cells; cancers of the endocrine glands, including cancer of the thyroid, pituitary gland and adrenal glands; skin cancers, including haemangiomas, melanomas and sarcomas, including Kaposi's sarcoma; tumours of the brain, nerves, eyes and meninges, including astrocytomas, gliomas, glioblastomas, retinoblastomas, neurinomas, neuroblastomas, schwannomas and meningiomas; solid tumours resulting from haematopoietic malignant tumours, including leukaemias, chloromas, plasmacytomas, fungoid mycosis, T-cell lymphoma or leukaemia, non-Hodgkin's lymphoma, malignant haemopathies and myelomas.

According to another of its aspects, the present invention relates to pharmaceutical compositions comprising, as active principle, a compound according to the invention. These pharmaceutical compositions comprise an effective dose of at least one compound according to the invention, or a pharmaceutically acceptable salt, a hydrate or solvate of the said compound, and at least one pharmaceutically acceptable excipient.

The said excipients are chosen, according to the pharmaceutical form and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its optional salt, solvate or hydrate, can be administered in unit administration form, as a mixture with conventional pharmaceutical excipients, to animals and man for the prophylaxis or treatment of the above disorders or diseases.

The appropriate unit administration forms comprise forms by the oral route, such as tablets, soft or hard gelatin capsules, powders, granules and oral solutions or suspensions, sublingual, buccal, intratracheal, intraocular or intranasal, by inhalation, administration forms, topical, transdermal, subcutaneous, intramuscular or intravenous administration forms, rectal administration forms and implants. Use may be made, for the topical application, of the compounds according to the invention in creams, gels, ointments or lotions.

The compounds of formula (I) above can be used at daily doses of 0.002 to 2 000 mg per kilogram of body weight of the mammal to be treated, preferably at daily doses of 0.1 to 300 mg/kg. In man, the dose can preferably vary from 0.02 to 10 000 mg per day, more particularly from 1 to 3 000 mg, depending on the age of the subject to be treated or the type of treatment: prophylactic or curative.

There may be specific cases where higher or lower dosages are appropriate; such dosages do not depart from the scope of the invention. According to usual practice, the dosage appropriate to each patient is determined by the doctor according to the method of administration and the weight and response of the said patient.

The present invention, according to another of its aspects, also relates to a method for the treatment of the pathologies indicated above which comprises the administration, to a patient, of an effective dose of a compound according to the invention, or one of its pharmaceutically acceptable salts or its hydrates or solvates.

According to the present invention, the compound or compounds of formula (I) can be administered in combination with one (or more) anticancer active principle(s), in particular antitumour compounds, such as alkylating agents, such as alkylsulphonates (busulfan), dacarbazine, procarbazine, nitrogen mustards (chlormethine, melphalan, chlorambucil), cyclophosphamide or ifosfamide; nitrosoureas, such as carmustine, lomustine, semustine or streptozocin; antineoplastic alkaloids, such as vincristine or vinblastine; taxanes, such as paclitaxel or taxotere; antineoplastic antibiotics, such as actinomycin; intercalating agents, antineoplastic antimetabolites, folate antagonists or methotrexate; purine synthesis inhibitors; purine analogues, such as mercaptopurine or 6-thioguanine; pyrimidine synthesis inhibitors, aromatase inhibitors, capecitabine or pyrimidine analogues, such as fluorouracil, gemcitabine, cytarabine and cytosine arabinoside; brequinar; topoisomerase inhibitors, such as camptothecin or etoposide; anticancer hormonal agonists and antagonists, including tamoxifen; kinase inhibitors, imatinib; growth factor inhibitors; antiinflammatories, such as pentosan polysulphate, corticosteroids, prednisone or dexamethasone; antitopoisomerases, such as etoposide, anthracyclines, including doxorubicin, bleomycin, mitomycin and mithramycin; anticancer metal complexes, platinum complexes, cisplatin, carboplatin or oxaliplatin; interferon-alpha, triphenyl thiophosphoramide or altretamine; antiangiogenic agents; thalidomide; immunotherapy adjuvants; or vaccines.

The present invention, according to another of its aspects, also relates to a method for the treatment of the pathologies indicated above which comprises administration, to a patient, of an effective dose of a compound according to the invention or one of its pharmaceutical acceptable salts or its hydrates or solvates.

What is claimed is:

1. A method for the treatment of a disease caused or exacerbated by the proliferation of tumour cells, which method comprises administering to a patient in need thereof an effective amount of a compound of formula (I):

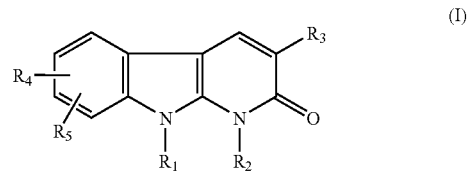

in which:
$R_1$ represents a hydrogen atom or a $(C_1-C_4)$alkyl group;
$R_2$ represents a hydrogen atom or a $(C_1-C_4)$alkyl group;
$R_3$ represents a monocyclic or bicyclic heterocyclic radical chosen from the group consisting of a pyridyl, an N-oxidopyridinio, a pyrazolyl, an (N-phenyl)pyrazolyl, an (N-halophenyl)pyrazolyl, a furyl, an indolyl, an (N-benzyl)indolyl, an (N-halobenzyl)indolyl, a benzothienyl and a benzofuryl, the said radicals being unsubstituted or substituted one or more times by a halogen atom or a methyl or methoxy group;
$R_4$ and $R_5$ are identical or different and each independently represent a hydrogen or halogen atom or a hydroxyl, hydroxymethyl, $(C_1-C_4)$alkyl, trifluoromethyl, $(C_1-C_4)$alkoxy, $(C_1-C_4)$alkoxycarbonyl or cyano group;

or an acid addition salt thereof, where the disease is selected from breast cancer, lung cancer, cancer of the small intestine, cancer of the colon, cancer of the rectum, cancer of the respiratory tract, cancer of the oropharynx, cancer of the hypopharynx, cancer of the oesophagus, liver cancer, stomach cancer, cancer of the bile ducts, cancer of the gall bladder, cancer of the pancreas, cancer of the urinary tract, cancer of the female genital tract, choriocarcinoma cancer, trophoblastic cancer, cancer of the male genital tract, tumors of the germinal cells, cancers of the endocrine glands, skin cancers, tumors of the brain, tumors of the nerves, tumours of the eyes, tumours of the meninges, and solid tumours resulting from haematopoietic malignant tumours.

2. The method according to claim 1, wherein for the compound of formula (I):
$R_1$ represents a hydrogen atom or a methyl group;
and/or $R_2$ represents a methyl group;
and/or $R_3$ represents a heterocyclic radical chosen from an N-oxidopyridinio, a pyridyl and a benzothienyl, the said radicals being unsubstituted or substituted one or more times by a halogen atom or a methyl or methoxy group;
and/or $R_4$ represents a methyl group;
and/or $R_5$ represents a hydrogen atom or a methyl group;

or an acid addition salt thereof.

3. The method according to claim 1, wherein the compound is selected from the group consisting of:
- 1,6-dimethyl-3-(pyridin-4-yl)-1,9-dihydro-2H-pyrido[2,3-b]indol-2-one;
- 1,6,9-trimethyl-3-(pyridin-4-yl)-1,9-dihydro-2H-pyrido[2,3-b]indol-2-one;
- 1,6-dimethyl-3-(1-oxidopyridin-4-io)-1,9-dihydro-2H-pyrido[2,3-b]indol-2-one;
- 3-(4,6-dimethylpyridin-2-yl)-1,6-dimethyl-1,9-dihydro-2H-pyrido[2,3-b]indol-2-one;
- 3-(1-benzothien-5-yl)-1,6-dimethyl-1,9-dihydro-2H-pyrido[2,3-b]indol-2-one;
- 3-(5-chloro-1-benzothien-3-yl)-1,6,9-trimethyl-1,9-dihydro-2H-pyrido[2,3-b]indol-2-one;
- 3-(1H-indol-1-yl)-1,6-dimethyl-1,9-dihydro-2H-pyrido[2,3-b]indol-2-one;
- 3-(3-chloropyridin-4-yl)-1,6-dimethyl-1,9-dihydro-2H-pyrido[2,3-b]indol-2-one;
- 3-(2,6-dimethoxypyridin-4-yl)-1,6-dimethyl-1,9-dihydro-2H-pyrido[2,3-b]indol-2-one; and
- 3-(2,6-dimethoxypyridin-4-yl)-1,6,9-trimethyl-1,9-dihydro-2H-pyrido[2,3-b]indol-2-one;

or an acid addition salt thereof.

4. The method according to claim 1 wherein the disease is selected from the group consisting of breast cancer, prostate cancer, colon cancer, skin cancer, and tumours of the brain.

5. The method according to claim 1 wherein the disease is breast cancer.

6. The method according to claim 1, wherein the compound is administered in combination with one or more anticancer active principle(s).

7. A method for the treatment of a disease caused or exacerbated by the proliferation of tumour cells, which method comprises administering to a patient in need thereof an effective amount of a compound selected from the group consisting of:
- 1,6,9-trimethyl-3-pyridin-3-yl-1,9-dihydro-pyrido[2,3-b]indol-2-one;
- 1,6,9-trimethyl-3-pyridin-4-yl-1,9-dihydro-pyrido[2,3-b]indol-2-one;
- 1,6,9-trimethyl-3-pyridin-2-yl-1,9-dihydro-pyrido[2,3-b]indol-2-one;
- 1,6-dimethyl-3-pyridin-4-yl-1,9-dihydro-pyrido[2,3-b]indol-2-one;
- 1,6,9-trimethyl-3-(1-methyl-1H-indol-3-yl)-1,9-dihydro-pyrido[2, 3-1)] indol-2-one;
- 1,6-dimethyl-3-pyridin-2-yl-1,9-dihydro-pyrido[2,3-b]indol-2-one;
- 1,6,9-trimethyl-3-(5-methyl-1-phenyl-1H-pyrazol-4-yl)-1,9-dihydro-pyrido[2,3-b]indol-2-one;
- 3-[1-(4-fluoro-benzyl)-1H-indol-3-yl]-1,6,9-trimethyl-1,9-dihydro-pyrido[2,3-b]indol-2-one;
- 3-benzo[b]thiophen-3-yl-1,6,9-trimethyl-1,9-dihydro-pyrido[2,3-b]indol-2-one;
- 3-benzo[b]thiophen-3-yl-1,6-dimethyl-1,9-dihydro-pyrido[2,3-b]indol-2-one;
- 3-(2,5-dimethyl-thiophen-3-yl)-1,6,9-trimethyl-1,9-dihydro-pyrido[2,3-b]indol-2-one;
- 3-(2,5-dimethyl-thiophen-3-yl)-1,6-dimethyl-1,9-dihydro-pyrido[2,3-b]indol-2-one;
- 3-(1-hydroxy-pyridin-4-yl)-1,6,9-trimethyl-1,9-dihydro-pyrido[2,3-b]indol-2-one;
- 3-(1-hydroxy-pyridin-4-yl)-1,6-dimethyl-1,9-dihydro-pyrido[2,3-b]indol-2-one;
- 3-(4,6-dimethyl-pyridin-2-yl)-1,6-dimethyl-1,9-dihydro-pyrido[2,3-b]indol-2-one;
- 1,6-dimethyl-3-pyridin-3-yl-1,9-dihydro-pyrido[2,3-b]indol-2-one;
- 3-(3-chloro-pyridin-4-yl)-1,6-dimethyl-1,9-dihydro-pyrido[2,3-b]indol-2-one;
- 3-(2,6-dimethoxy-pyridin-4-yl)-1,6-dimethyl-1,9-dihydro-pyrido[2,3-b]indol-2-one;
- 3-(2,6-dimethoxy-pyridin-4-yl)-1,6,9-trimethyl-1,9-dihydro-pyrido[2,3-b]indol-2-one;
- 3-(5-chloro-benzo[b]thiophen-3-yl)-1,6-dimethyl-1,9-dihydro-pyrido[2,3-b]indol-2-one;
- 3-(5-chloro-benzo[b]thiophen-3-yl)-1,6,9-trimethyl-1,9-dihydro-pyrido[2, 3-1)] indol-2-one;
- 1,6-dimethyl-3-(3-methyl-benzo[b]thiophen-2-yl)-1,9-dihydro-pyrido[2, 3-1)] indol-2-one;
- 1,6,9-trimethyl-3-(3-methyl-benzo[b]thiophen-2-yl)-1,9-dihydro-pyrido[2, 3-1)]indol-2-one;
- 3-benzo[b]thiophen-5-yl-1,6-dimethyl-1,9-dihydro-pyrido[2,3-b]indol-2-one;
- 3-benzo[b]thiophen-5-yl-1,6,9-trimethyl-1,9-dihydro-pyrido[2,3-b]indol-2-one;
- 3-indol-1-yl-1,6-dimethyl-1,9-dihydro-pyrido[2,3-b]indol-2-one; and
- 3-indol-1-yl-1,6,9-trimethyl-1,9-dihydro-pyrido[2,3-b]indol-2-one;

or an acid addition salt thereof, wherein the disease is selected from breast cancer, lung cancer, cancer of the small intestine, cancer of the colon, cancer of the rectum, cancer of the respiratory tract, cancer of the oropharynx, cancer of the hypopharynx, cancer of the oesophagus, liver cancer, stomach cancer, cancer of the bile ducts, cancer of the gall bladder, cancer of the pancreas, cancer of the urinary tract, cancer of the female genital tract, choriocarcinoma cancer, trophoblastic cancer, cancer of the male genital tract, tumors of the germinal cells, cancers of the endocrine glands, skin cancers, tumors of the brain, tumors of the nerves, tumours of the eyes, tumours of the meninges, and solid tumours resulting from haematopoietic malignant tumours.

* * * * *

UNITED STATES PATENT AND TRADEMARK OFFICE
CERTIFICATE OF CORRECTION

PATENT NO. : 7,816,368 B2  
APPLICATION NO. : 12/252647  
DATED : October 19, 2010  
INVENTOR(S) : Bernard Bourrie et al.

Page 1 of 1

It is certified that error appears in the above-identified patent and that said Letters Patent is hereby corrected as shown below:

On the first page, in column 2, under "Other Publications", line 5, delete "Assesing" and insert -- Assessing --, therefor.

In column 6, line 22, delete "ppm" and insert -- ppm: --, therefor.

In column 7, line 6, delete "ppm" and insert -- ppm: --, therefor.

In column 11, line 66, delete "s" and insert -- s: --, therefor.

In column 12, line 32, delete "s" and insert -- s: --, therefor.

In column 13, line 25, delete "s" and insert -- s: --, therefor.

In column 22, line 66-67, delete "haemopathies" and insert -- hemopathies --, therefor.

In column 25, line 47, in claim 7, delete "[2,3-1)]" and insert -- [2,3-b] --, therefor.

In column 26, line 26, in claim 7, delete "[2,3-1)]" and insert -- [2,3-b] --, therefor.

In column 26, line 28, in claim 7, delete "[2,3-1)]" and insert -- [2,3-b] --, therefor.

In column 26, line 30, in claim 7, delete "[2,3-1)]" and insert -- [2,3-b] --, therefor.

Signed and Sealed this  
Twenty-fourth Day of May, 2011

David J. Kappos  
*Director of the United States Patent and Trademark Office*